United States Patent [19]

Ripley et al.

[11] 4,228,506
[45] Oct. 14, 1980

[54] CHARTER WITH AUTOMATIC EDITING

[75] Inventors: John A. Ripley, Newport Beach; Donald C. Woods, Lompoc; James Kaine, Santa Ana, all of Calif.

[73] Assignee: Del Mar Avionics, Irvine, Calif.

[21] Appl. No.: 959,091

[22] Filed: Nov. 9, 1978

[51] Int. Cl.³ ............................................. G06F 3/05
[52] U.S. Cl. .................................. 364/415; 364/575; 364/900
[58] Field of Search ............... 364/445, 447, 421, 422, 364/900, 200, 519-520, 572, 574, 575

[56] References Cited

U.S. PATENT DOCUMENTS

| 3,940,742 | 2/1976 | Hudspeth et al. | 364/900 |
|---|---|---|---|
| 3,970,996 | 7/1976 | Yasaka et al. | 364/900 |
| 3,994,285 | 11/1976 | Doll | 364/575 X |
| 4,006,737 | 2/1977 | Cherry | 364/417 X |
| 4,053,951 | 10/1977 | Hudspeth, et al. | 364/415 |
| 4,070,708 | 1/1978 | Smallcombe et al. | 364/575 |
| 4,110,730 | 8/1978 | Varecka et al. | 364/574 X |

*Primary Examiner*—Edward J. Wise
*Attorney, Agent, or Firm*—Smyth, Pavitt, Siegemund, Jones & Martella

[57] ABSTRACT

An intelligent printer-plotter for use with a source of time-correlated digital systolic and diastolic blood pressure data and heart rate data receives, stores, analyzes, and edits the data, producing tables of data and graphs having a particular format. The charter smooths the data by a moving average technique and includes modes which permit the operator to edit the data manually or to command the charter to perform the editing automatically. In the automatic editing mode, the data are tested against pre-established criteria. Data not meeting the criteria is flagged so that it can be passed over in subsequent calculation and printing operations; however, the flagged data is not destroyed, but is retained in a memory to permit subsequent re-examination and to permit verification of the editing process.

9 Claims, 23 Drawing Figures

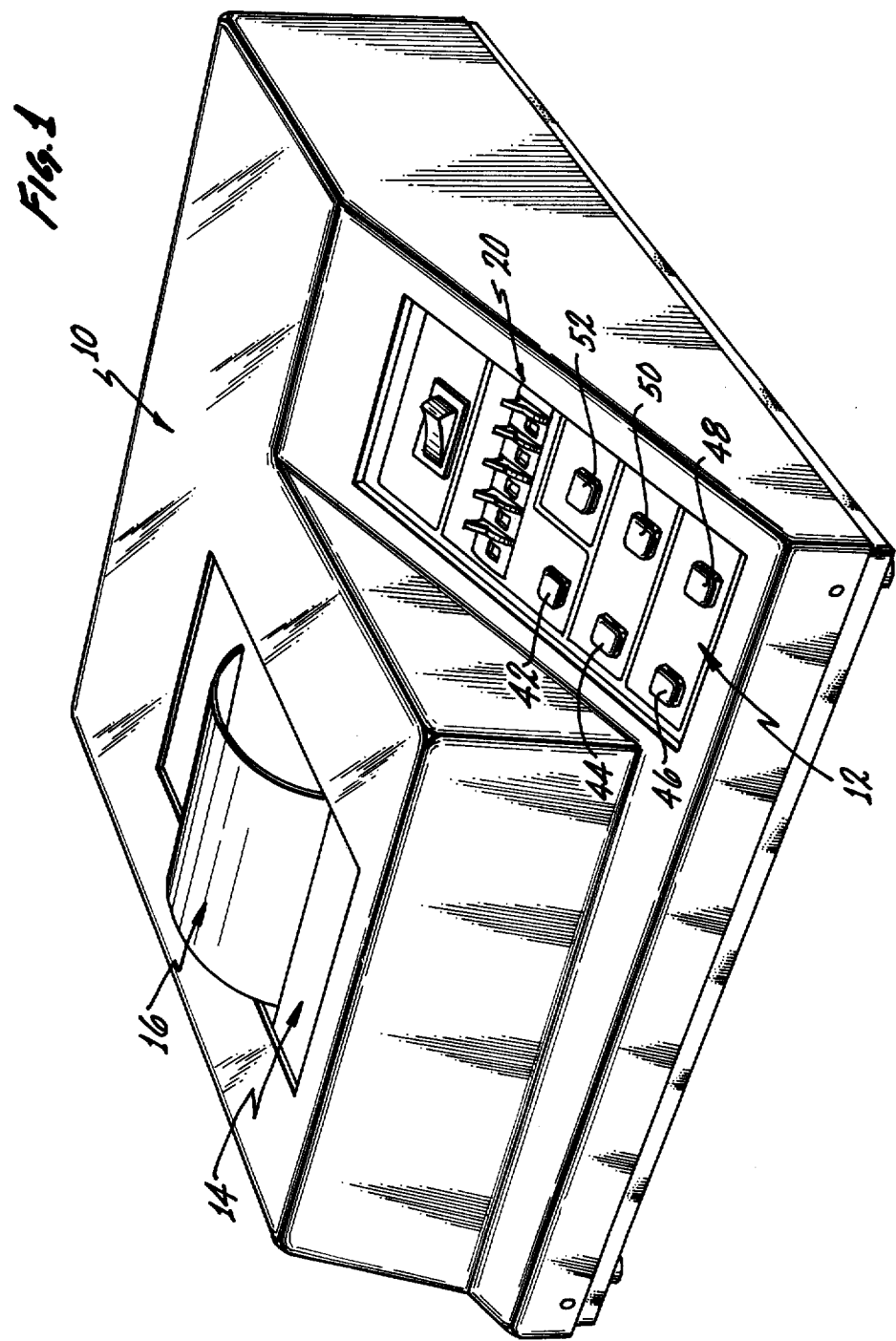

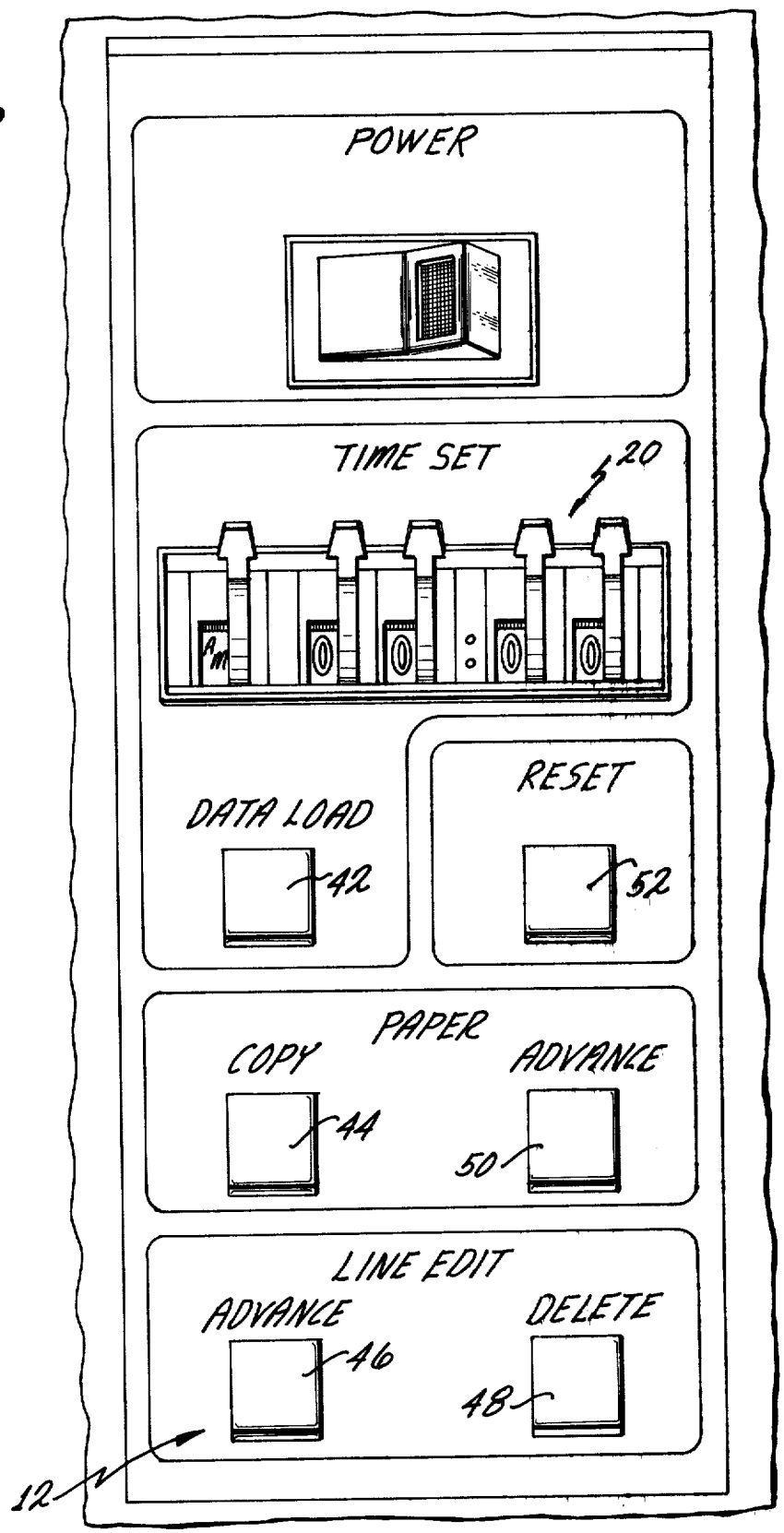

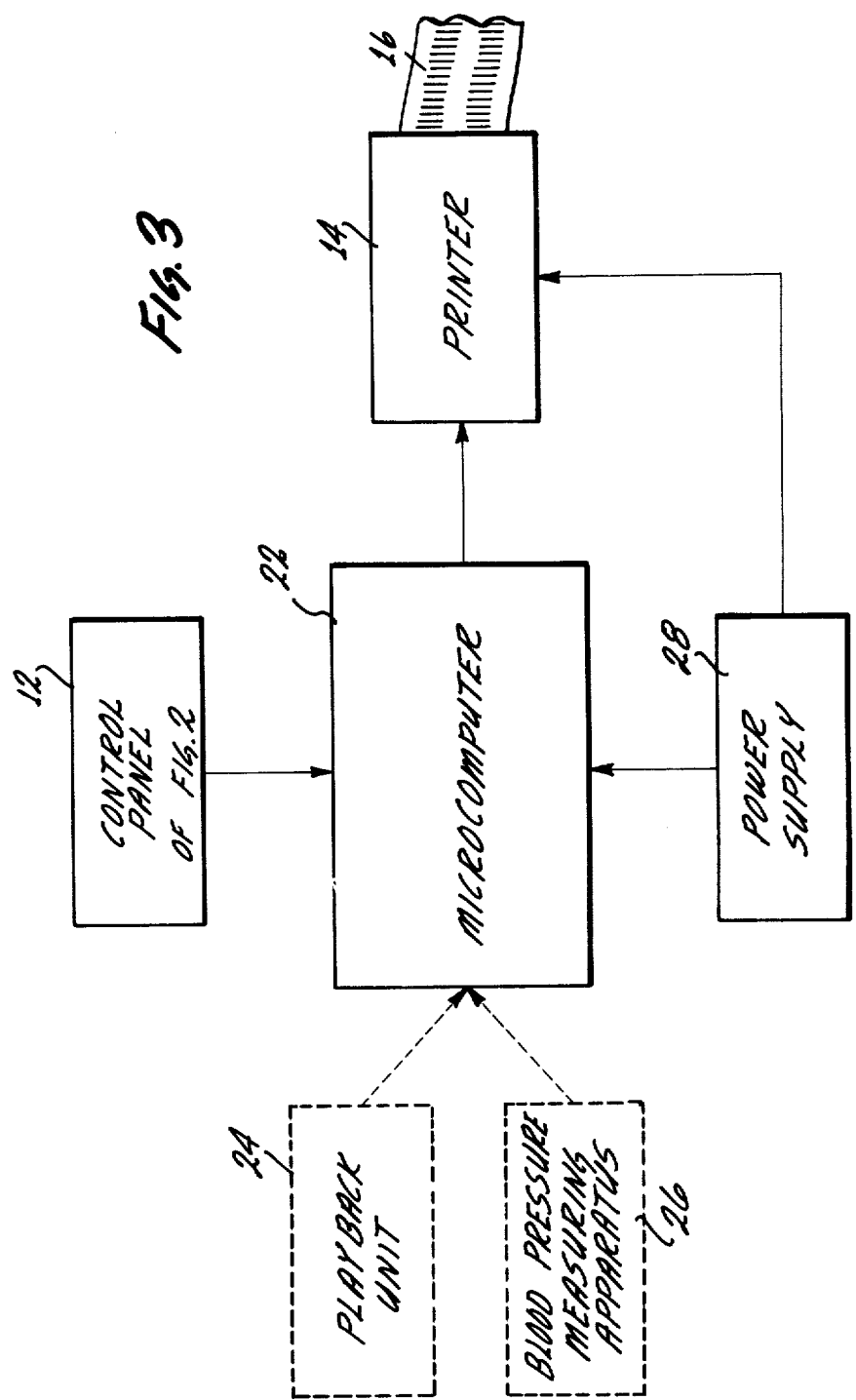

FIG. 4a

```
NAME........................................
DATE........................................
PHYSICIAN...................................
START TIME:  2:04A

TIME     SYS-     DIAS-    HEART    PR RATE
         TOLIC    TOLIC    RATE     PRODUCT

2:08A    191       20       74      14134
2:11     179      128       78      13962
2:13     192      131       76      14592
2:15     180      128       84      15120
2:17     161      129       79      12719
2:30     198      125       83      16434
2:38     172      111       84      14448
2:46     171      108       79      13509
2:53     171      118       73      12483
3:01     184      125       79      14536
3:09     177      120       79      13983
3:17     167      111       77      12859
3:24     176      173       83      14608
3:32     160      104       78      12480
3:40     197      107       76      14972
3:48     221      114       76      16796
3:56     166      127       94      15604
4:04     160      123       79      12640
4:12     180      106       79      14220
4:19     183      127       97      17751
4:27     174      118      103      17922
4:34     149      117      109      16241
4:42     184       93      105      19320
4:49     103      106      117      12051
4:57      96      102      114      10944
5:04     162      104      125      20250
5:11     134      105       97      12998
5:19     132      117      102      13464
5:26     156      143       99      15444
5:34     144      115       99      14256
5:41     151      116       98      14798
5:49     146      116       97      14162
5:57     144       98      103      14832
6:04     137      116      108      14796
6:11     126      114       98      12348
6:19     153      123       96      14688
6:26     160      117       97      15520
6:34     154      100       95      14630
6:41     170      119       98      16660
6:49     184      114      121      22264
6:56      84      101      102       8568
7:04      93      106      112      10416
7:11      89       97      101       8989
7:18     167      118      101      15030
7:26     146      119       94      13724
7:33     149      111      106      15794
7:41     159      100      105      16695
7:48      92      117      101       9292
7:56     128      104      105      13440
8:03      89      118      101       8989
8:11     149      114       96      14304
8:19      85      104      105       8925
8:26     158       99       95      15010
8:33     137      106       88      12056
8:41     173      106      101      17473
8:49     231       95       98      22638
8:56     154      105       97      14938
9:03     164       87       91      14924
9:11     170      123       87      14790
9:19     219      208      103      22557
9:26     153      119       96      14688
9:33     166      110       98      16268
9:40     166      108      115      19090
9:48     213      130      115      24495
```

```
NAME........................................
DATE........................................
PHYSICIAN...................................
START TIME:  2:04A

TIME    SYS-    DIAS-   HEART   PR RATE
        TOLIC   TOLIC   RATE    PRODUCT
```

| TIME | SYSTOLIC | DIASTOLIC | HEART RATE | PR RATE PRODUCT |
|---|---|---|---|---|
| 2:09A | 191 | 20 | 74 | 14134 |
| 2:11 | 179 | 108 | 78 | 13962 |
| 2:13 | 192 | 131 | 76 | 14592 |
| 2:15 | 180 | 128 | 84 | 15120 |
| 2:17 | 161 | 129 | 79 | 12719 |
| 2:30 | 198 | 125 | 83 | 16434 |
| 2:38 | 172 | 111 | 84 | 14448 |
| 2:46 | 171 | 108 | 79 | 13509 |
| 2:53 | 171 | 118 | 73 | 12483 |
| 3:01 | 184 | 125 | 79 | 14536 |
| 3:09 | 177 | 120 | 79 | 13983 |
| 3:17 | 167 | 111 | 77 | 12859 |
| 3:24 | * | | | |
| 3:32 | 160 | 104 | 78 | 12480 |
| 3:40 | 197 | 107 | 76 | 14972 |
| 3:48 | 221 | 114 | 76 | 16796 |
| 3:56 | 166 | 127 | 94 | 15604 |
| 4:04 | 160 | 123 | 79 | 12640 |
| 4:12 | 180 | 106 | 79 | 14220 |
| 4:19 | 183 | 127 | 97 | 17751 |
| 4:27 | 174 | 118 | 103 | 17922 |
| 4:34 | 149 | 117 | 109 | 16241 |
| 4:42 | 184 | 99 | 105 | 19320 |
| 4:49 | * | | | |
| 4:57 | * | | | |
| 5:04 | 162 | 104 | 125 | 20250 |
| 5:11 | 134 | 105 | 97 | 12998 |
| 5:19 | 132 | 117 | 102 | 13464 |
| 5:26 | 156 | 143 | 99 | 15444 |
| 5:34 | 144 | 115 | 99 | 14256 |
| 5:41 | 151 | 116 | 98 | 14798 |
| 5:49 | 146 | 116 | 97 | 14162 |
| 5:57 | 144 | 98 | 103 | 14832 |
| 6:04 | 137 | 116 | 108 | 14796 |
| 6:11 | 126 | 114 | 98 | 12348 |
| 6:19 | 153 | 123 | 96 | 14688 |
| 6:26 | 160 | 117 | 97 | 15520 |
| 6:34 | 154 | 100 | 95 | 14630 |
| 6:41 | 170 | 119 | 98 | 16660 |
| 6:49 | 184 | 114 | 121 | 22264 |
| 6:56 | * | | | |
| 7:04 | * | | | |
| 7:11 | * | | | |
| 7:18 | 167 | 118 | 90 | 15030 |
| 7:26 | 146 | 119 | 94 | 13724 |
| 7:33 | 149 | 111 | 106 | 15794 |
| 7:41 | 159 | 100 | 105 | 16695 |
| 7:48 | * | | | |
| 7:56 | * | | | |
| 8:03 | * | | | |
| 8:11 | 149 | 114 | 96 | 14304 |
| 8:18 | * | | | |
| 8:26 | 158 | 99 | 95 | 15010 |
| 8:33 | 137 | 106 | 88 | 12056 |
| 8:41 | 173 | 106 | 101 | 17473 |
| 8:49 | 231 | 95 | 98 | 22638 |
| 8:56 | 154 | 105 | 97 | 14938 |
| 9:03 | 164 | 87 | 91 | 14924 |
| 9:11 | 170 | 123 | 87 | 14790 |
| 9:18 | 219 | 208 | 103 | 22557 |
| 9:26 | 153 | 119 | 96 | 14688 |
| 9:33 | 166 | 110 | 98 | 16268 |
| 9:40 | 166 | 108 | 115 | 19090 |
| 9:48 | 213 | 130 | 115 | 24495 |

*Fig.4d*

| TIME | SYS-TOLIC | DIAS-TOLIC | HEART RATE | PR RATE PRODUCT |
|---|---|---|---|---|
| 2:08A | 191 | 20 | 74 | 14134 |
| 2:08 | * | | | |
| 2:11 | 179 | 128 | 78 | 13962 |
| 2:13 | 192 | 131 | 76 | 14592 |
| 2:15 | 180 | 128 | 84 | 15120 |
| 2:17 | 161 | 129 | 79 | 12719 |
| 2:30 | 198 | 125 | 83 | 16434 |
| 2:38 | 172 | 111 | 84 | 14448 |
| 2:46 | 171 | 108 | 79 | 13509 |
| 2:53 | 171 | 118 | 73 | 12483 |
| 3:01 | 184 | 125 | 79 | 14536 |
| 3:09 | 177 | 120 | 79 | 13983 |
| 3:17 | 167 | 111 | 77 | 12859 |
| 3:24 | * | | | |
| 3:32 | 160 | 104 | 78 | 12480 |
| 3:40 | 197 | 107 | 76 | 14972 |
| 3:48 | 221 | 114 | 76 | 16796 |
| 3:56 | 166 | 127 | 94 | 15604 |
| 4:04 | 160 | 123 | 79 | 12640 |
| 4:12 | 180 | 106 | 79 | 14220 |
| 4:19 | 183 | 127 | 97 | 17751 |
| 4:27 | 174 | 118 | 103 | 17922 |
| 4:34 | 149 | 117 | 109 | 16241 |
| 4:42 | 184 | 93 | 105 | 19320 |
| 4:49 | * | | | |
| 4:57 | * | | | |
| 5:04 | 162 | 104 | 125 | 20250 |
| 5:11 | 134 | 105 | 97 | 12998 |
| 5:19 | 132 | 117 | 102 | 13464 |
| 5:26 | 156 | 143 | 99 | 15444 |
| 5:34 | 144 | 115 | 99 | 14256 |
| 5:41 | 151 | 116 | 98 | 14798 |
| 5:49 | 146 | 116 | 97 | 14162 |
| 5:57 | 144 | 98 | 103 | 14832 |
| 6:04 | 137 | 116 | 108 | 14796 |
| 6:11 | 126 | 114 | 98 | 12348 |
| 6:19 | 153 | 123 | 96 | 14688 |
| 6:26 | 160 | 117 | 97 | 15520 |
| 6:34 | 154 | 100 | 95 | 14630 |
| 6:41 | 170 | 119 | 98 | 16660 |
| 6:49 | 184 | 114 | 121 | 22264 |
| 6:56 | * | | | |
| 7:04 | * | | | |
| 7:11 | 167 | 118 | 90 | 15030 |
| 7:18 | 146 | 119 | 94 | 13724 |
| 7:26 | 149 | 111 | 106 | 15794 |
| 7:33 | 159 | 100 | 105 | 16695 |
| 7:41 | * | | | |
| 7:48 | * | | | |
| 7:56 | * | | | |
| 8:03 | * | | | |
| 8:11 | 149 | 114 | 96 | 14304 |
| 8:18 | * | | | |
| 8:26 | 158 | 99 | 95 | 15010 |
| 8:33 | 137 | 106 | 88 | 12056 |
| 8:41 | 173 | 106 | 101 | 17473 |
| 8:49 | 231 | 95 | 98 | 22638 |
| 8:56 | 154 | 105 | 97 | 14938 |
| 9:03 | 164 | 87 | 91 | 14924 |
| 9:11 | 170 | 123 | 87 | 14790 |
| 9:18 | 219 | 208 | 103 | 22557 |
| 9:18 | * | | | |
| 9:26 | 153 | 119 | 96 | 14688 |
| 9:33 | * | | | |
| 9:33 | 166 | 110 | 98 | 16268 |
| 9:40 | * | | | |
| 9:40 | 166 | 108 | 115 | 19090 |
| 9:48 | * | | | |
| 9:48 | 213 | 130 | 115 | 24495 |
| 9:48 | * | | | |

FIG. 4g

```
NAME..................................
DATE..................................
PHYSICIAN.............................
START TIME:    2:04A

TIME      SYS-      DIAS-     HEART     PR RATE
          TOLIC     TOLIC     RATE      PRODUCT

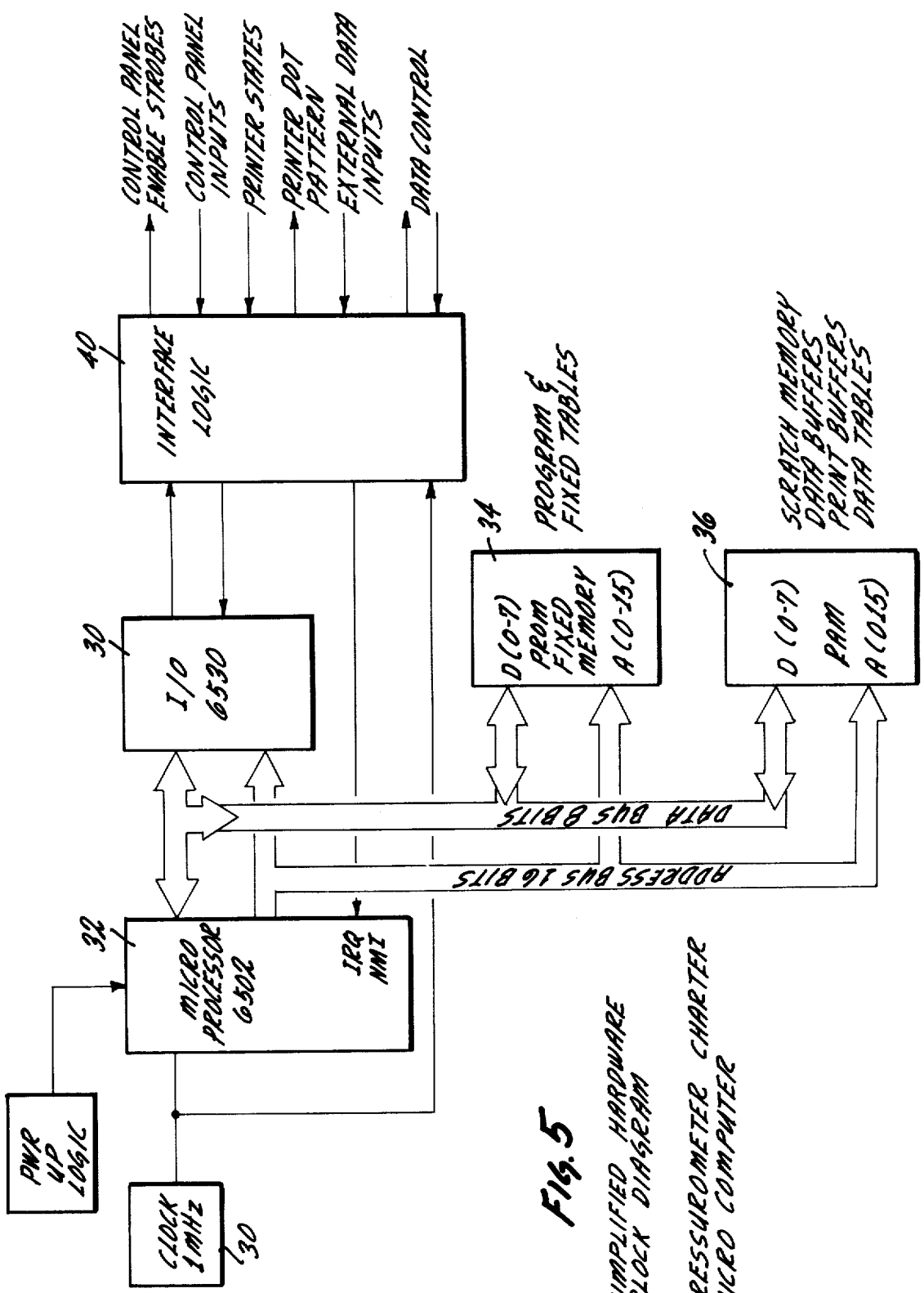

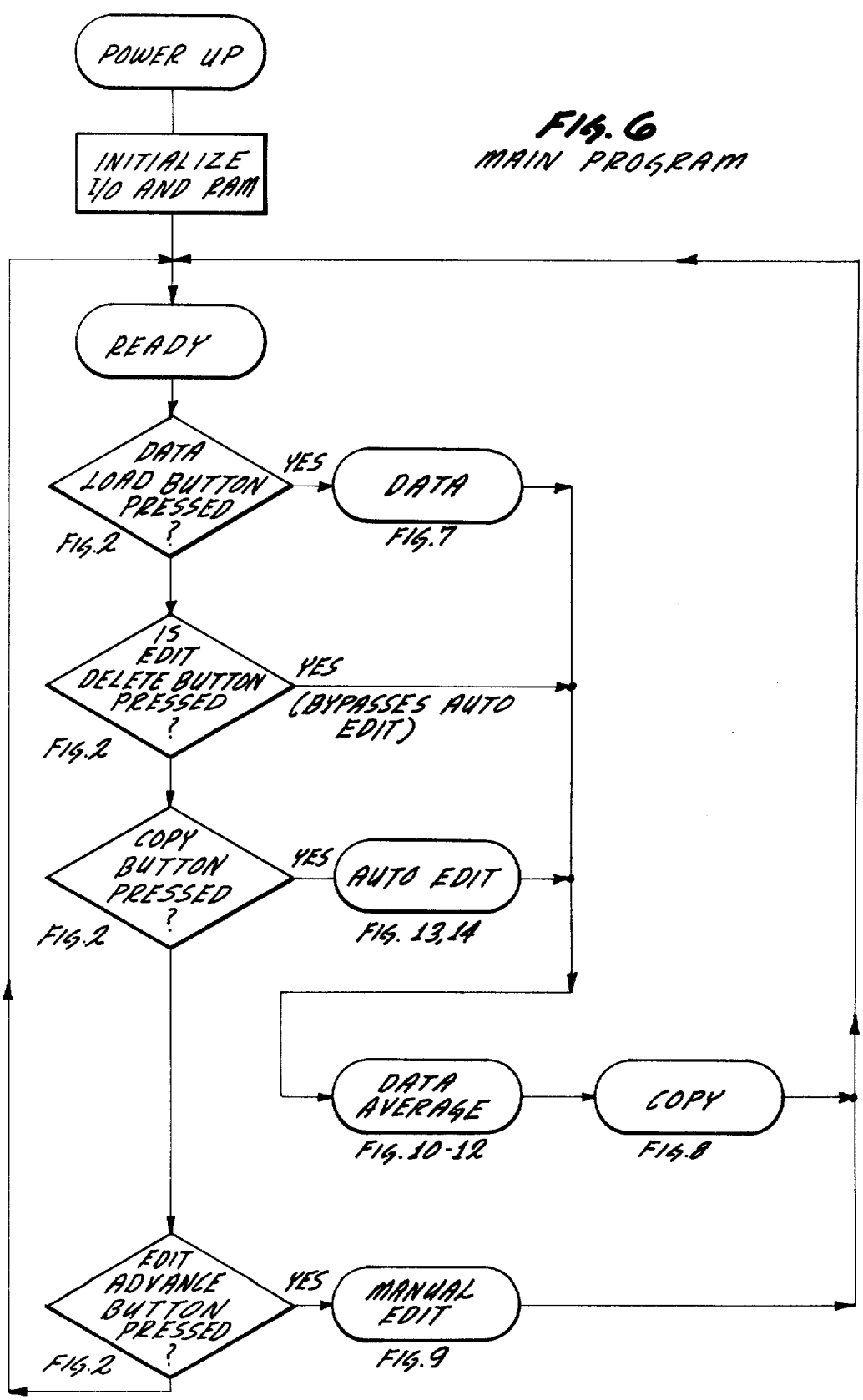

CHARTER WITH AUTOMATIC EDITING

BACKGROUND OF THE INVENTION

1. Field of the Invention

The present invention is in the field of medical electronics, and more specifically relates to an intelligent printer-plotter for presenting medical data in the form of printed tables and plotted graphs, and which is capable of smoothing the data by averaging it, and which further provides for editing of the data automatically and manually.

2. The Prior Art

In U.S. patent application Ser. No. 796,893 filed May 16, 1977, for Blood Pressure Monitoring System by Squires et al. there is described a portable device and a portable recorder to be worn by a patient to permit the measuring and recording of the patient's blood pressure and ECG signals over an extended period of time, such as 24 hours, as the patient engages in his daily program of activities. The value of such ambulatory monitoring is widely recognized and it is particularly useful when the symptoms are present only sporadically. Typically, in such a system, the systolic and diastolic blood pressures are measured at 7.5 minute intervals and recorded on a magnetic tape along with a continuous recording of the ECG signals.

The recorded tape is played back on an apparatus of the type disclosed in U.S. Pat. No. 4,073,011 issued Feb. 7, 1978, to Cherry et al. That playback device can be provided with a blood pressure data decoder and with a heart rate trend computer (as described in the aforementioned application of Squires et al.) to permit the blood pressure and heart rate data to be read from the magnetic tape and converted to a standardized signal format. The playback unit also produces timing signals in relation to the amount of tape played back, which permits the time of the various measurements to be determined. Thus, the playback unit provides as an output, time correlated data words representing values of systolic blood pressure, diastolic blood pressure and heart rate, along with timing signals. To be useful to a physician, these electrical signals must be reduced to a printed form such as a table or a graph.

It would, of course, be possible to use a printer or a charter of the kind known in the art to produce a table or chart of the raw data; unequestionably, such a graphical output would be helpful. However, upon reflection it can be seen that a simple printer or plotter is not the most desirable means for producing the graphical record. It is well known that intervention by the patient may cause fluctuations to appear in the raw data when the physiological variables are in fact substantially constant, and it is also known that some variability in the physiological variables is to be expected as the patient pursues his daily activities. In most applications, the physician is not concerned with these transient phenomena, but instead is interested in the longer-term variations. Thus, it would appear desirable to filter the data prior to plotting it to eliminate values which are clearly erroneous or impossible and to average the readings to eliminate the short-term fluctuations.

SUMMARY OF THE INVENTION

The present invention is an intelligent printer/plotter which gives the operator greater control of the output data presented. Like the simpler plotters, the present invention can print and plot the raw data. But, the capabilities of the present invention extend far beyond those of a simple data plotter. The present invention smooths the data by time-averaging the values. In a preferred embodiment, the operator can command the present invention to automatically edit the data by filtering out and deleting data which can be recognized as erroneous. Further, the present invention includes means to permit the operator to review the raw data and then to manually delete values he deems to be erroneous. The charter of the present invention retains the raw data in storage even after the data has been edited manually or automatically. This feature permits verification that the editing was done correctly, and permits subsequent re-examination of the raw data if that is suggested by the edited data.

The charter of the present invention obtains blood pressure data, heart rate data and clock signals from the playback as inputs. The data is ordered with respect to time in the sense that, typically, a set of systolic, diastolic and heart rate readings is received at 7.5-minute invervals throughout an extended period of time. The present invention stores these sets of data in a storage device so that when commanded, the charter can produce tabular print-outs and charts of heart rate and systolic and diastolic blood pressure readings versus time of day when the measurement was performed. The present invention also calculates and presents the pressure-rate product (systolic blood pressure times heart rate) in tabular and graphical form. Further, the charter of the present invention performs a coincident 3-reading moving average on the measured values to smooth the data, so that trends can more easily be observed and measured.

In the charter of the present invention, the operator can manually edit the data in a line advance/delete mode, or alternatively the operator can jump to any location to manually delete data.

When commanded by the operator, the charter of the present invention will automatically edit the data, deleting data which is recognized as being erroneous. This automatic editing feature frees the operator from spending a considerable amount of time deleting erroneous data manually. The operator can select whether edited or unedited is to be printed out, and, if desired, both edited and unedited data can be printed out in sequence.

In accordance with the present invention, the raw data is not destroyed in either the automatic or manual editing modes, but instead is retained so that it may be used for further studies or to verify that the editing was correctly done.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective view of the external features of the charter of the present invention;

FIG. 2 is a plan view of the control panel of the charter of FIG. 1;

FIG. 3 is a block diagram showing the overall organization of the charter;

FIG. 4a is an exemplary copy of a portion of the printed report produced by the charter, showing the raw data and the double product printed versus time;

FIG. 4d is an exemplary copy of the report produced by the charter, showing the auto-edited data in tabular form;

FIG. 4g is an exemplary copy of the report produced during the manual editing operation;

FIG. 4h is an exemplary copy of a tabular printout produced to verify the correctness of the manual editing operation;

FIG. 5 is a block diagram of the hardware of the microcomputer used in the charter;

FIG. 6 is a flow chart showing the main program of the microcomputer of FIG. 5;

DETAILED DESCRIPTION OF THE PREFERRED EMBODIMENT

Figure 4B:
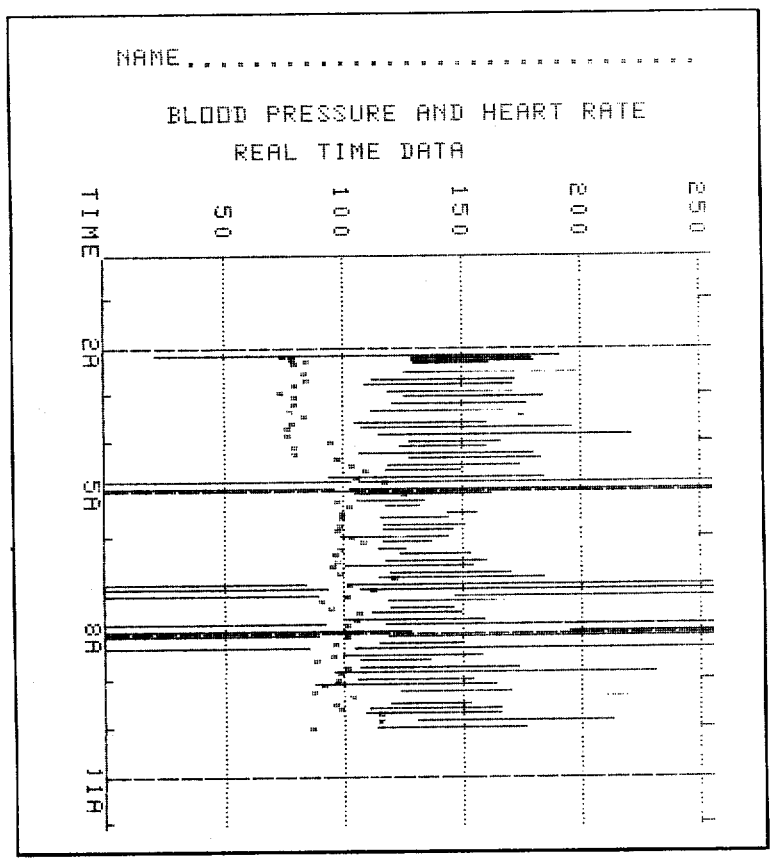
FIG. 4b is an exemplary copy of the report produced by the charter and showing a graph of blood pressure and heart rate versus time.

Turning now to the drawings, in which like numerals are used to denote the same parts, there is shown in FIG. 1 a perspective view of the external features of the charter 10 of the present invention. The charter 10 includes a control panel 12 shown more clearly in FIG. 2 and a printer head 14 used for producing an output record 16 on which are displayed tables of data and graphs, similar to those shown in FIGS. 4a-4h.

The charter of the present invention provides high-speed write-outs of ambulatory blood pressure and heart rate data in both numerical and graphical form. The data is received from a playback unit which scans the magnetic tapes produced during the ambulatory recording session and produces from the tape electrical signals representing the data and having a predetermined signal format.

The blood pressure measuring apparatus used during the ambulatory recording session may be pre-programmed to initiate blood pressure measurements at intervals of 7.5, 15, or 30 minutes as selected by the physician. The time interval chosen establishes the interval of the tabular data and graphs of the output record 16, although the present invention can also respond to patient-activated blood pressure measurement cycles and can assign to them the correct time of day.

In operation, data received from the playback unit is stored in a memory in the charter of the present invention. Upon completion of the playback, the charter 10 produces a three segment write-out at a speed of two lines per second. Normally, the operator would elect to have the charter 10 automatically edit the data to delete information which is obviously erroneous. In most cases, this feature eliminates the need for visual review of the write-out for errors, and thereby eliminates the need for manual deletion. Deletions are indicated on the write-out 16 by asterisks printed adjacent the time reading. A control 44 of FIG. 2 on the control panel 12 permits the production of one or more additional edited copies.

The charter of the present invention is simple to operate, with all of the controls conveniently mounted on a compact sloping front control panel 12, as shown in FIG. 2. The POWER, DELETE, and COPY pushswitches light up when pressed so that the operating mode can be readily identified. Five digit-switches 20 are provided for entering the time of day at which the ambulatory recording was begun. This initial time of day is then updated by the clock signals generated by the playback unit.

The write-outs are presented on electrosensitive paper which incorporates an aluminized conducting circuit over a dark coating. Current pulses applied to the paper burn off the top surface exposing the dark curving and providing easy-to-read dots which make up the characters being plotted. The printing is thus accomplished without fumes or residue, and the paper is impervious to fingerprints. Such coated papers are known in the art.

As shown in FIG. 3, the charter includes a microcomputer 22 which can accept signals from the playback unit 24 or, in an alternative embodiment from a blood pressure measuring apparatus 26. Neither the playback unit 24 or the blood pressure measuring apparatus 26 is part of the present invention. The microcomputer 22 is controlled by an operator through the use of the control panel 12, which is also shown in FIG. 2. A power supply 28 supplies operating power to the microcomputer 22 as well as to the printer 14. The microcomputer 22, as will be seen below, includes means for receiving, storing, analyzing, and editing the data and produces electrical signals which are applied to the printer 14 to cause it to produce the output record 16.

FIGS. 4a-4h exemplify the output record 16 produced by the charter. As seen in FIG. 4a, the charter identifies the patient and produces the necessary headings at the beginning of the record. The first part of the record is shown in FIG. 4a and consists of a tabular write-out of the raw systolic, diastolic and heart rate data. The charter also prints in the right-hand column the produce of the systolic reading multiplied by the heart rate.

In FIG. 4b the data of the table of FIG. 4a is shown plotted by the printer 14.

Figure 4C:
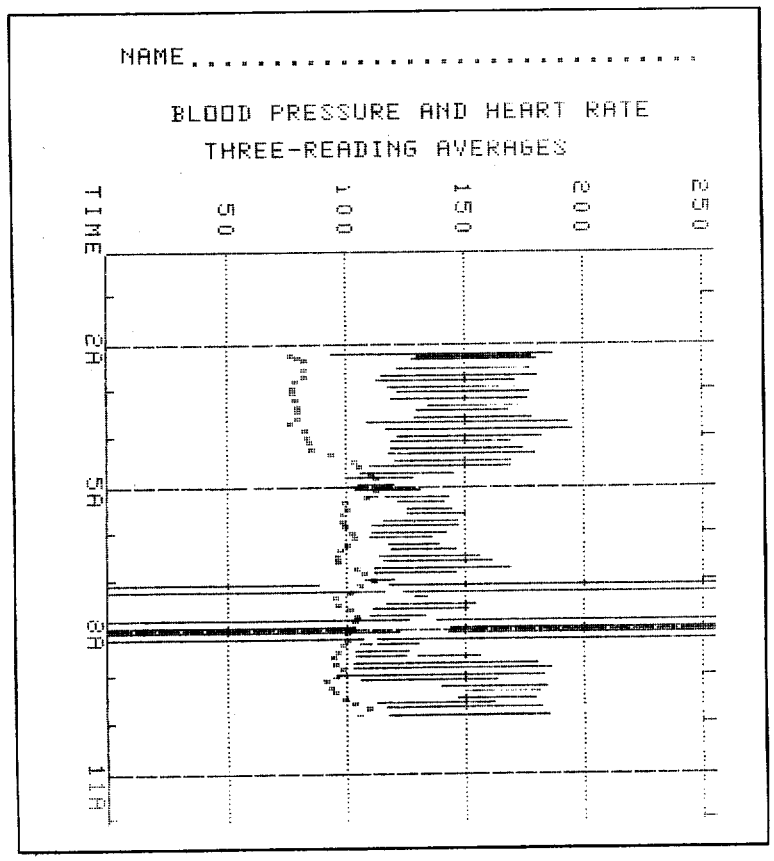
FIG. 4c is an exemplary copy of a portion of the record produced by the charter showing a chart of the moving averages of blood pressure and heart rate versus time.
Figure 4E:
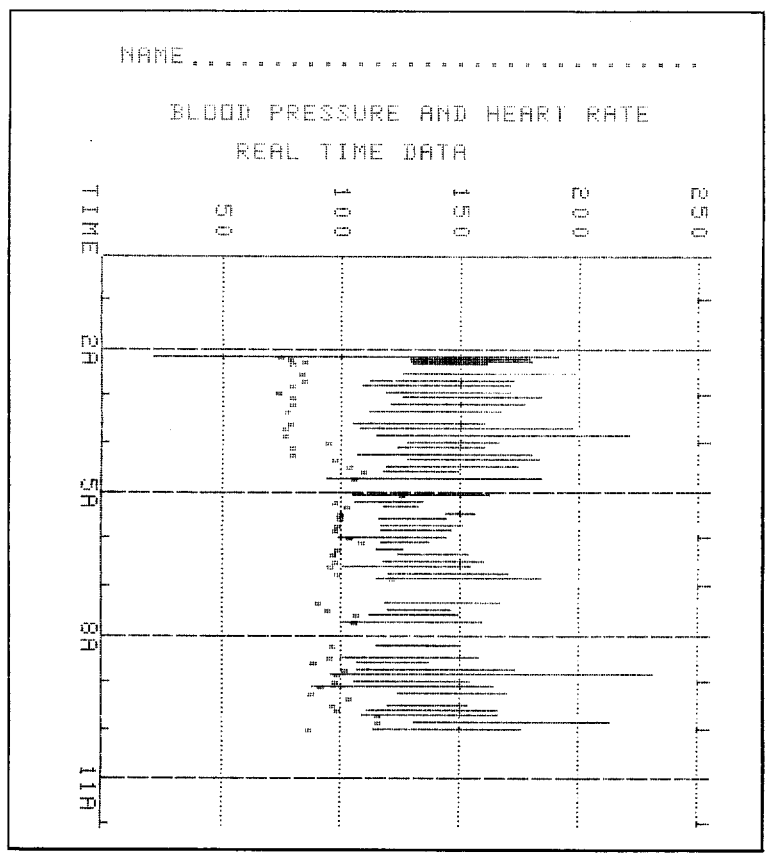
FIG. 4e is an exemplary copy of the report showing a graph of the data of FIG. 4d.
Figure 4F:
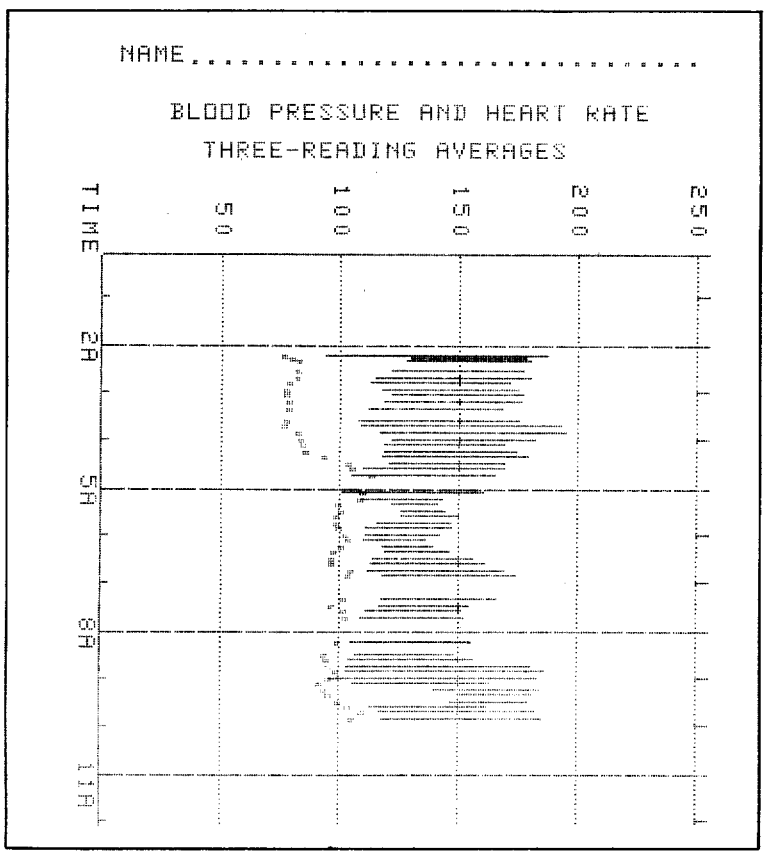
FIG. 4f is an exemplary copy of the report showing a graph of the data of FIG. 4d after the data has been averaged.

The microcomputer 22 also includes circuitry for smoothing the raw data of FIGS. 4a and 4b by performing a moving average calculation on each of the columns of data shown in FIG. 4a, to produce the graph shown in FIG. 4c. It should be noted that the data shown in FIG. 4c is smoother than that shown in FIG. 4b and is therefore more effective in helping to identify the underlying trends in the data.

Next, the operator elects to command the charter to perform an automatic editing of the data. The auto-edited data is printed in tabular form in FIG. 4d and plotted in FIG. 4e. The averaged auto-edited data is plotted in FIG. 4f.

It should be noted that the charter deleted the data at time 3:24 because the difference between the systolic and diastolic readings was too small, and the data at times 4:49 and 4:57 were deleted because the systolic reading was less than the diastolic reading. The initial reading, at 2:08 was not deleted because the diastolic reading was not less than 20 mmHg.

Upon perusing the auto-edited data in this example, the operator has decided that the first reading (at time 2:08) should be deleted and that all readings after 9:11 should be deleted (a medication having been administered at that time).

Figure 4I:
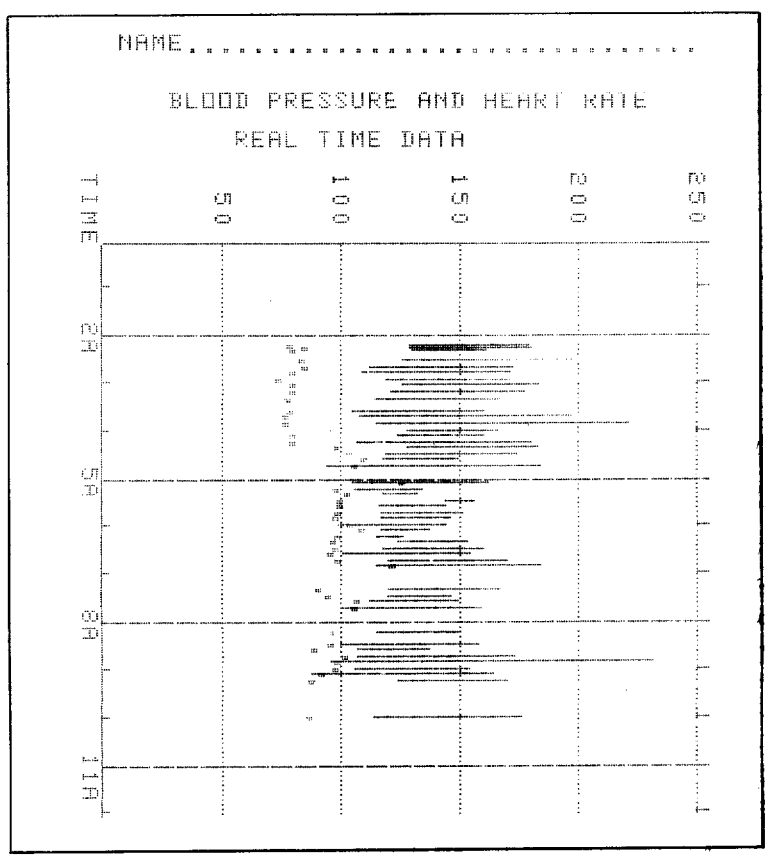
FIG. 4i is an exemplary copy of a graph of the data of FIG. 4h.
Figure 4J:
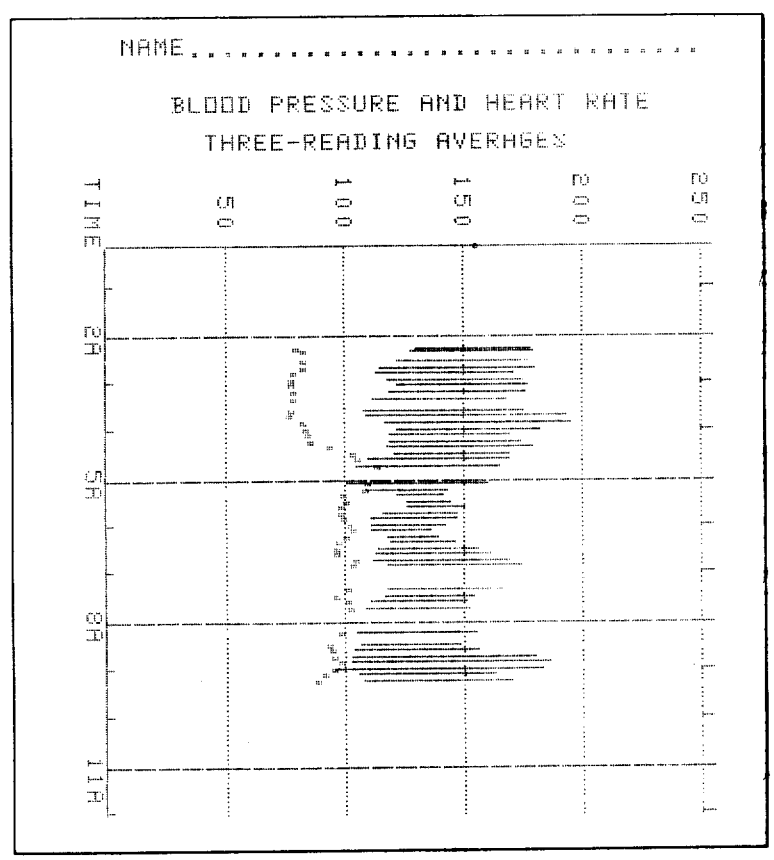
FIG. 4j is an exemplary copy of a graph of the data of FIG. 4h after the data has been averaged.

Therefore as shown in FIG. 4g, the operator enters the manual edit mode, printing the data line-by-line and deleting the chosen lines. The operator then elects to print the data, which has been edited both automatically and manually, as shown in FIG. 4h, to verify that the deletions have been made correctly. The data of FIG. 4h is then plotted in the graphs of FIGS. 4i and 4j.

FIG. 5 is a block diagram of the microcomputer 22 of FIG. 3. Operation of the microcomputer is synchronized by a 1 MHz clock 30 and a Model No. 6502 microprocessor 32 available commerically from the MOS Technology Corporation of Norristown, PA.

The microcomputer utilizes a read only memory (PROM) to store its program instructions and fixed tables, and utilizes a random access memory (RAM) 36 for the data buffers, data tables, scratch pad memory, and printer buffers. Communications between the microcomputer and the control panel, the printer, and the source of data pass through the input-output (I/O) device 30 which is a Model No. 6530 available commercially from the MOS Technology Corporation. Interrupt signals are generated by the interface logic 40 to assist the microcomputer to synchronize with real time events.

After the charter has been connected to the source of data, the DATA LOAD button of FIG. 2 is depressed by the operator to transfer the data from the source into the RAM memory 36 of FIG. 5. Upon actuation, the switch will illuminate, and the printer will execute one line advance of the paper. The switch will be extinguished briefly each time a blood pressure and heart rate reading received from the data source is processed by the charter. When the COPY button 44 of FIG. 2 is thereafter depressed, the charter will produce the printed table and charts of the type shown in FIGS. 4a–4c, or the printer will write NO DATA if there was no acceptable data. Actuation of the EDIT DELETE button 46 of FIG. 2 by the operator will cause the COPY lamp to light and allow unedited data to be printed for subsequent review and manual editing by the operator. The COPY button 48 will, when depressed, initiate automatic editing.

The manual edit mode is entered by depressing the EDIT ADVANCE button. Alternately depressing the EDIT ADVANCE button 46 and the EDIT DELETE button 48 the operator can advance the charter manually through the tabulated data allowing deletion of selected lines. The manually edited data can then be printed by actuation of the COPY button 44. The PAPER ADVANCE button 50 is used for advancing the paper and is used mainly when the roll of paper is changed or to allow space between selected groups of data. The RESET button 52 is used to interrupt any of the above modes of operation, returning the microcomputer to the READY mode. Actuation of the various control buttons 42–52 on the control panel 12 of FIG. 2 determines which of the several programs or routines stored in the PROM memory 34 of FIG. 5 will be executed by the microcomputer. FIGS. 6–14 are flow charts which describe the various programs in sufficient detail to permit one skilled in the art to write a set of detailed instructions implementing the program.

FIG. 6 is a flow chart showing the main program which is followed by the microcomputer 22 of FIG. 3. When the POWER switch 54 of FIG. 2 is actuated, the power supply 28 of FIG. 3 applies power to the microcomputer 22 and the printer 14. This initiates the main program of FIG. 6, which begins with the operation of initializing the input-output device 30 and the RAM 36 of FIG. 5. Following this initialization step, the microcomputer pauses at a READY mode, awaiting further commands by the operator, applied via the control panel 12. Assuming the charter is connected to the source of data, the operator presses the DATA LOAD button 42 of FIG. 2, and this causes the microcomputer to enter the DATA routine of FIG. 7. That routine loads the incoming data into the RAM 36 of FIG. 5. Once the data has been loaded into the RAM 36, the microcomputer initiates the DATA AVERAGE routine of FIGS. 10–12.

Figure 10:
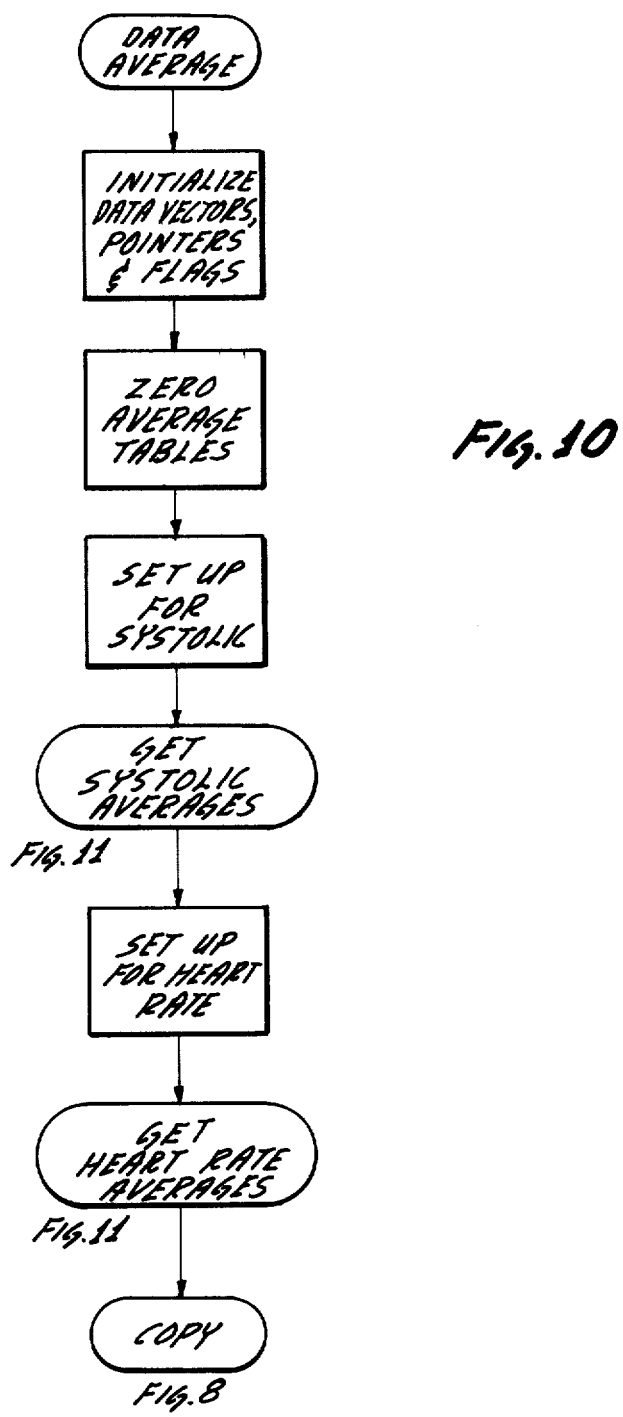
FIG. 10 is a flow chart of the DATA AVERAGE portion of the program.
Figure 11:
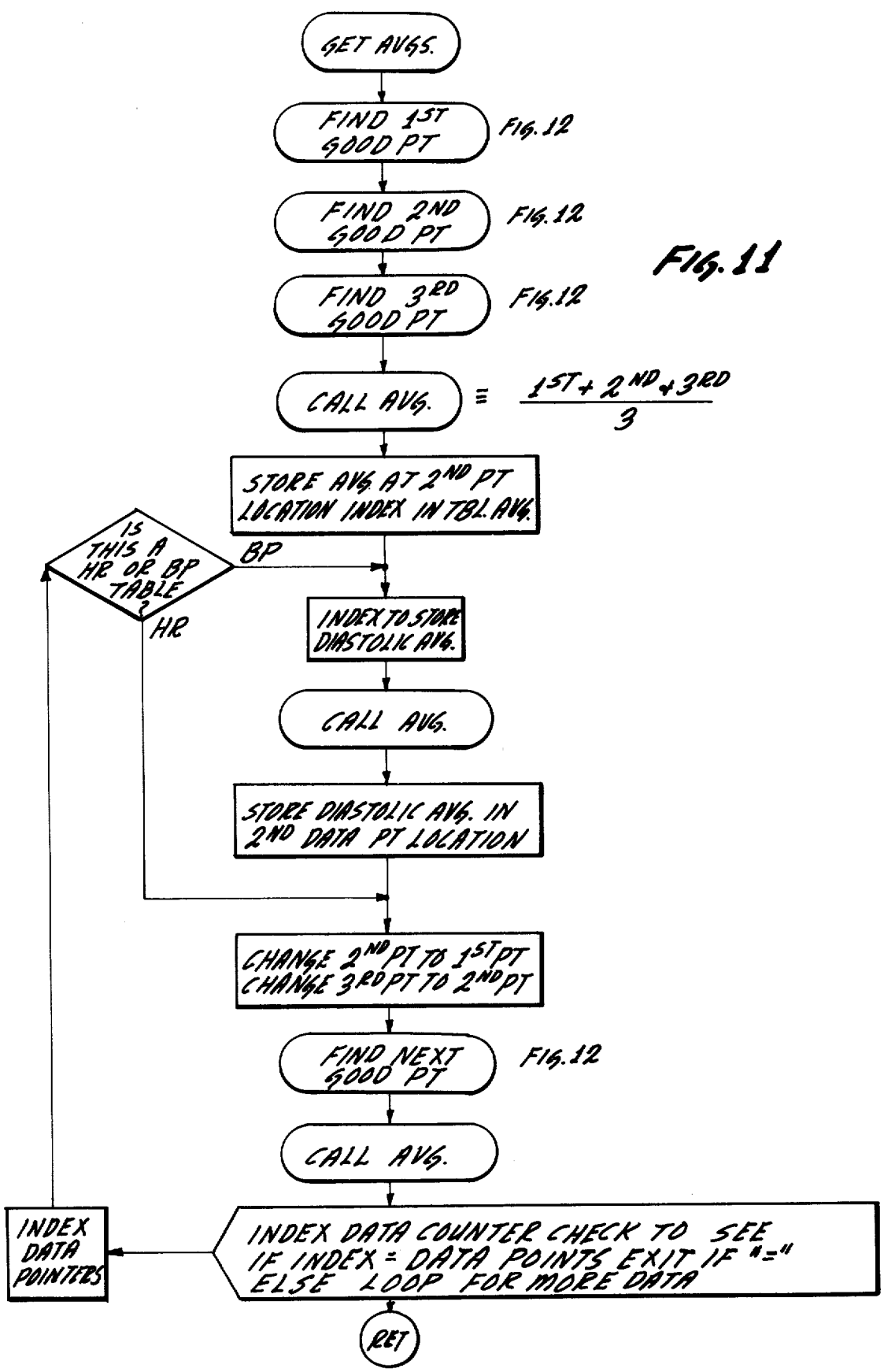
FIG. 11 is a flow chart of a subroutine used in the DATA AVERAGE routine.
Figure 12:
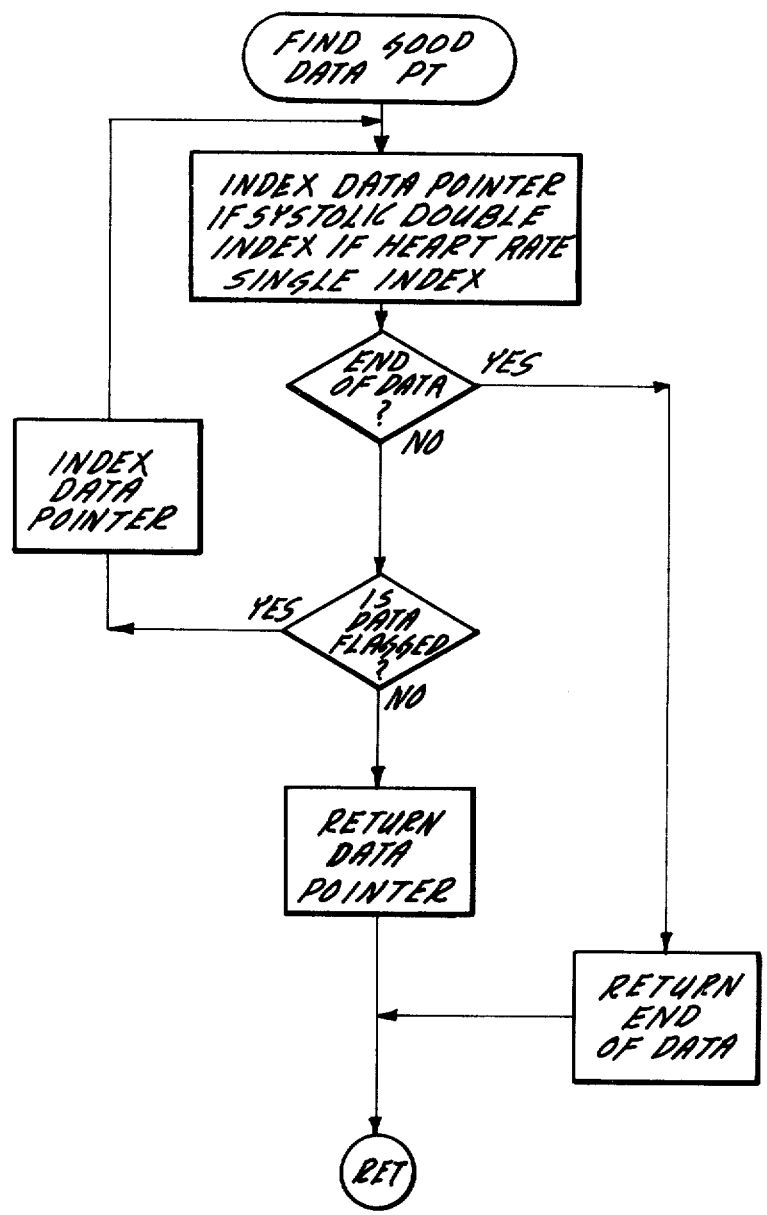
FIG. 12 is a flow chart of a subroutine used in averaging the data.

In a preferred embodiment, the DATA AVERAGE routine of FIGS. 10–12 performs a coincident three-reading moving average operation on the data, storing the results in another section of the RAM 36.

Figure 8:
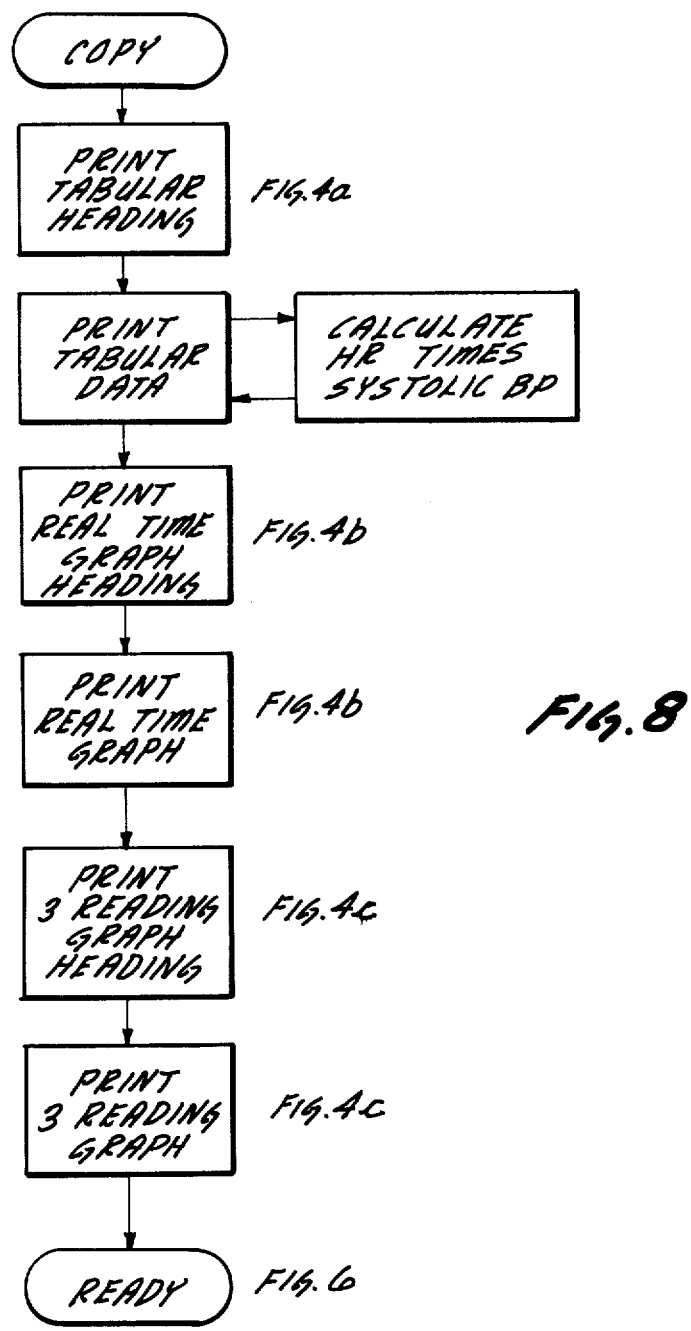
FIG. 8 is a flow diagram of the COPY portion of the program of FIG. 6.

Thereafter, the microcomputer proceeds to the COPY routine shown in FIG. 8, which provides for printing of the tables and graphs similar to those shown in FIGS. 4a–4c. Upon completion of the COPY routine of FIG. 8, the microcomputer returns to the READY mode to await further commands. At this point, the operator has been provided with tables and charts of the unedited data in both its raw form and in smoothed form. On the basis of this data, the operator can decide whether he wishes to edit the data, and if so, whether the editing should be performed automatically by the charter or manually by the operator using the charter.

Figure 9:
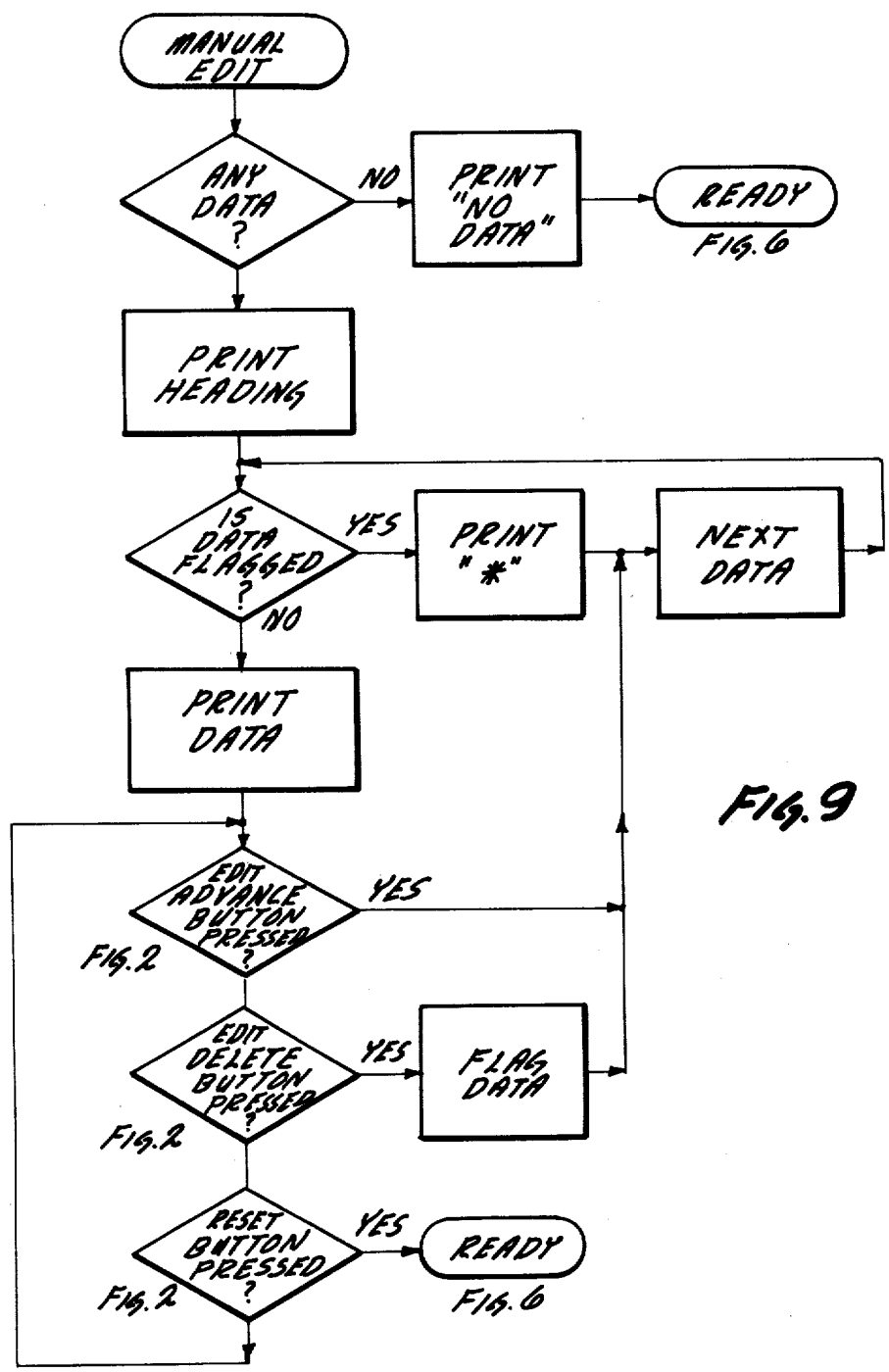
FIG. 9 is a flow chart of the MANUAL EDIT portion of the program of FIG. 6.

If the operator elects the automatic editing mode, he commands the microprocessor to initiate automatic editing by depressing the COPY button 44 of FIG. 2. This causes the microcomputer to execute the automatic editing routine shown in FIGS. 13, 14. The portion of the routine shown in FIG. 14 embodies the data filter, which is seen to consist of a series of pre-established conditions all of which must be satisfied if the data is to be regarded as not being erroneous. If any of the conditions fails to obtain, the data is flagged to indicate that it is judged to be erroneous and is therefore disgarded in the further printing and calculating operations, such as what is shown in FIGS. 9 and 12.

Figure 13:
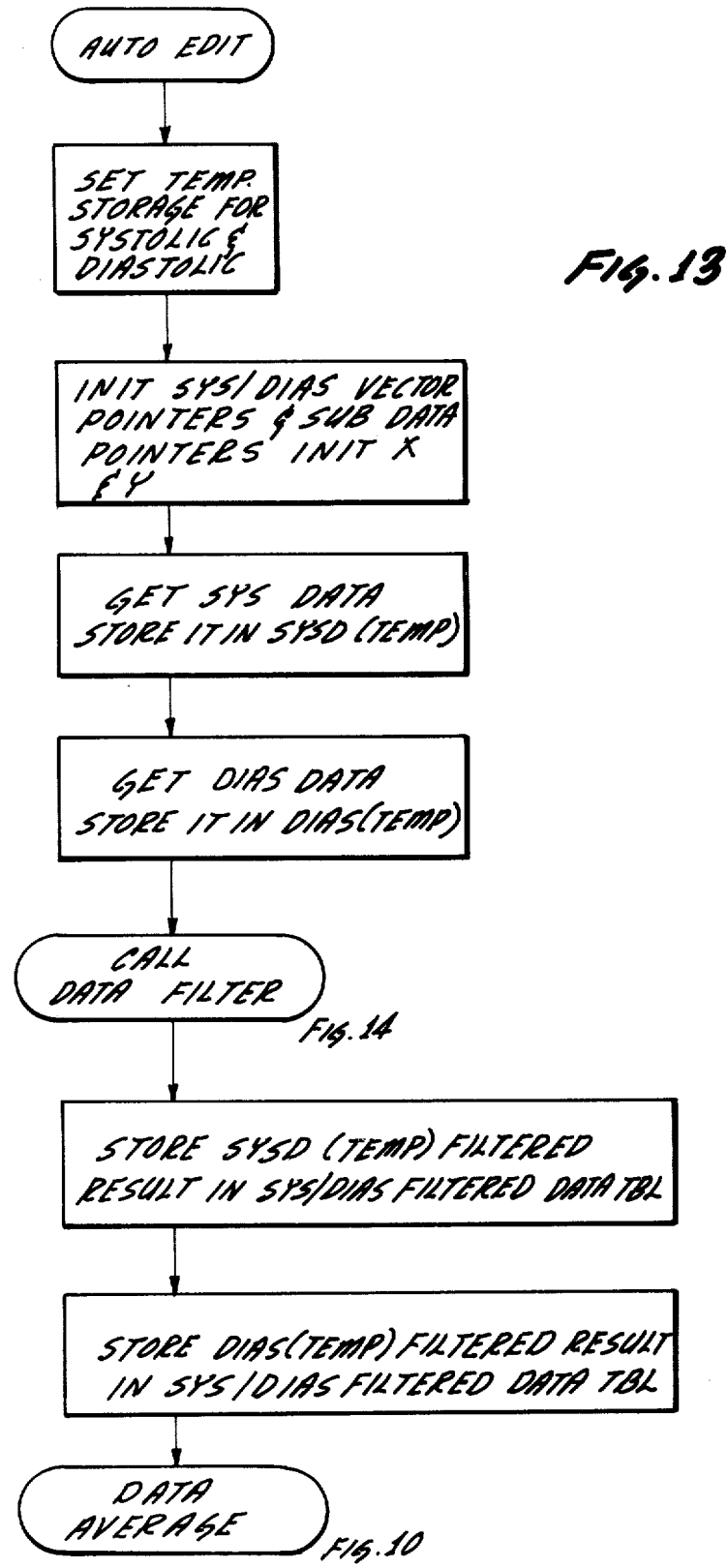
FIG. 13 is a flow chart of the AUTO EDIT routine used in the automatic editing feature of the charter; and, FIG. 14 is a flow chart of the DATA FILTER subroutine used in the AUTO EDIT portion of the program.

The automatic editing routine of FIG. 13 leads to execution of the DATA AVERAGE and COPY routines, which produces tabular and graphical presentations of the edited data in both its unsmoothed and smoothed forms.

Instead of electing the automatic editing routine, the operator could have elected to edit the data manually, and this decision could have been implemented by depressing the LINE EDIT ADVANCE button 46 of FIG. 2. This causes the microcomputer to initiate the MANUAL EDIT routine shown in FIG. 9. That routine causes successive lines of tabular data to be printed, viewed by the operator, and deleted if so desired by depressing the EDIT DELETE button 48 of FIG. 2, which flags the data to be deleted. When the operator has finished the manual editing operation, he depresses the RESET button 52 of FIG. 2 which returns the microcomputer to the READY mode.

Figure 7:
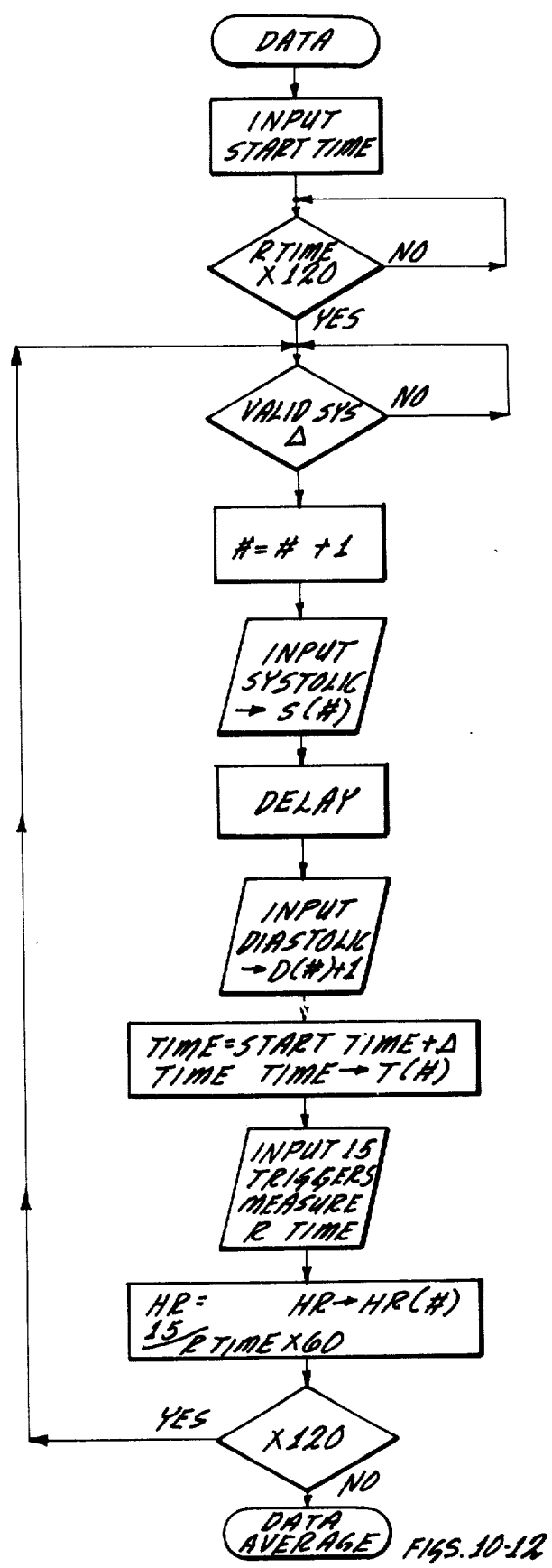
FIG. 7 is a flow chart of the DATA portion of the program of FIG. 6.

It should be noted that the DATA routine of FIG. 7 calculates the heart rate by measuring the amount of real time required for fifteen heart beats to occur, and then dividing this time in seconds into nine hundred (i.e., 15×60). The DATA routine of FIG. 7 also calculates the product of the systolic blood pressure and the substantially coincident value of the heart rate.

The MANUAL EDIT routine of FIG. 9 prints out the first line of the table of data and permits the operator to decide whether or not it should be flagged as being erroneous. If the operator depresses the EDIT ADVANCE button, the data is judged to be valid and the next line of data is printed. On the other hand, if the operator decides that the data is erroneous, when he presses the EDIT DELETE button, a flag will be written in a storage area associated with the erroneous data, and, thus flagged, the data will be disregarded in further operations, and will be replaced by an asterisk in subsequent printouts.

The DATA AVERAGE routine of FIGS. 10-12 merely advances through the tabulated data locating three successive "good" (unflagged) data points, and upon finding three such points calculates an unweighted three-point coincident moving average. Thereafter, the first of the three data points is discarded and a fourth point is sought.

Figure 14:
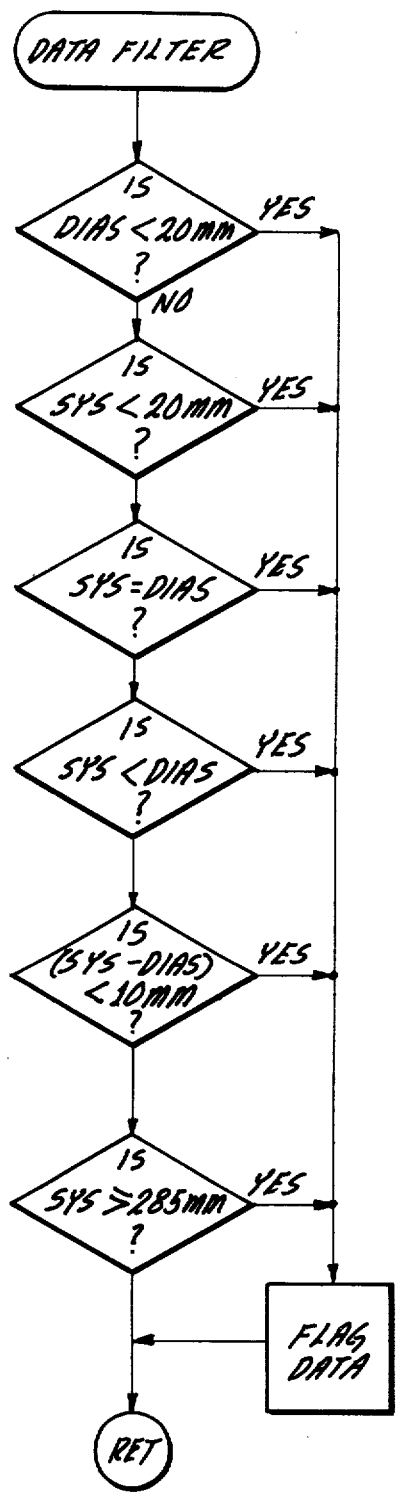

The AUTO EDIT routine of FIGS. 13 and 14 advances through the tabulated data performing a number of tests on the substantially concurrent systolic and diastolic readings to determine if those readings are valid.

In a preferred embodiment the data filter employs the following criteria:

IF DIASTOLIC<20 mmHg→REJECT DATA

IF SYSTOLIC<20 mmHg→REJECT DATA

IF SYSTOLIC=DIASTOLIC→REJECT DATA

IF SYSTOLIC<DIASTOLIC→REJECT DATA

IF SYSTOLIC minus DIASTOLIC<10 mmHg→REJECT DATA

IF SYSTOLIC≧245 mmHg→REJECT DATA

The criteria used in the automatic editing routine is stored in the PROM 34 and can be changed by reprogramming.

Thus, there has been described an intelligent printer-plotter which includes an automatic editing feature as well as a manual editing capability. The operator can elect to use either the manual or the automatic mode. Regardless of which mode is chosen, the raw data is not destroyed by the editing process, but is merely flagged so that it can be disregarded in operations requiring edited data. The charter of the present invention also performs smoothing and arithmetic operations on the data.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. A charter for use with a source of time correlated digital systolic and diastolic blood pressure data and heart rate data, for receiving, storing, analyzing, and editing the data, and for producing tables and charts having a particular format for displaying under control of an operator in edited and unedited form both the data as received from the source and the analyzed data, said charter comprising in combination:

first storage means connected to the source of data for storing words of data when they are received from the source of data, and including flag storage locations associated with each of the words of data for storing as required a flag along with each word of data;

automatic editing means connected to said first storage means and operable in response to an edit command to edit by testing stored words of data to determine whether the stored words of data meet certain pre-established qualifications and to write a flag in the flag storage location associated with each of the stored words of data if the stored words of data do not meet the pre-established qualifications, so that edited data words meeting the pre-established qualifications can subsequently be recognized by the absence of a flag in their associated flag storage locations, both the edited and unedited data being retained in said first storage means after editing for selected use including verification and evaluation of the operation of said automatic editing means.

2. The charter of claim 1 further comprising:

manual editing means connected to said first storage means and operable under control of an operator for writing a flag in the flag storage location associated with a selected stored word of data.

3. The charter of claim 2 further comprising:

printer means connected to said first data storage means and displaying under control of the operator the unedited stored data words in a particular format to enable the operator to select a data word to be deleted, and displaying under control of the operator the edited stored data words to permit the operator to verify that the editing has been done correctly, both the edited and unedited data being retained thereafter in said first storage means for selected use including subsequent re-examination of the unedited data by the operator.

4. The charter of claim 1 wherein said pre-established qualifications include a range of acceptable magnitudes, a flag being written by said automatic editing means in the flag storage location associated with a stored word of data if the magnitude of the stored word of data is not within the range of acceptable magnitudes.

5. The charter of claim 1 wherein said pre-established qualifications include pre-established relations between substantially concurrent systolic and diastolic blood pressure data, a flag being written by said automatic editing means in the flag storage location associated with the stored systolic and diastolic blood pressure data if any of the pre-established relations does not obtain.

6. The charter of claim 1 further comprising:
arithmetical means connected to said first storage means for averaging stored words of systolic blood pressure data, for averaging stored words of diastolic blood pressure data, and for averaging stored words of heart rate data, and operable to employ in the averaging the unedited or the edited data as selected by the operator.

7. The charter of claim 6 further comprising:
printer means connected to said arithmetical means for printing in numerical form and for plotting in graphical form the averaged data in the edited or unedited form selected by the operator.

8. The charter of claim 1 further comprising:
arithmetical means connected to said first storage means for calculating the product of substantially concurrent systolic blood pressure and heart rate data.

9. The charter of claim 8 further comprising:
printer means connected to said arithmetical means for printing in numerical form and for plotting in graphical form the calculated product.

* * * * *